(12) United States Patent
Lawson

(10) Patent No.: US 7,479,290 B2
(45) Date of Patent: Jan. 20, 2009

(54) SOLVENT EXTRACTION PROCESS

(75) Inventor: Chris Lawson, Reading (GB)

(73) Assignee: Glycomed Sciences Limited, Grand Cayman (KY)

( * ) Notice: Subject to any disclaimer, the term of this patent is extended or adjusted under 35 U.S.C. 154(b) by 0 days.

(21) Appl. No.: 10/490,333

(22) PCT Filed: Sep. 30, 2002

(86) PCT No.: PCT/EP02/10946

§ 371 (c)(1),
(2), (4) Date: Mar. 18, 2004

(87) PCT Pub. No.: WO03/029269

PCT Pub. Date: Apr. 10, 2003

(65) Prior Publication Data

US 2004/0249138 A1 Dec. 9, 2004

(30) Foreign Application Priority Data

Sep. 28, 2001 (EP) .................................. 01123458

(51) Int. Cl.
*A61K 36/00* (2006.01)
(52) U.S. Cl. ..................................................... 424/725
(58) Field of Classification Search .................. 424/725
See application file for complete search history.

(56) References Cited

U.S. PATENT DOCUMENTS 3,960,839 A   6/1976  Guerrero ................. 260/210.5
6,214,803 B1 *  4/2001  Kuo et al. ..................... 514/26
7,078,063 B2 *  7/2006  Kuo ............................ 424/725
2004/0259814 A1 * 12/2004  Shahid ........................ 514/26

FOREIGN PATENT DOCUMENTS

WO    WO91/10743    7/1991
WO    WO00/61153    10/2000

OTHER PUBLICATIONS

Cham et al. "HPLC of Glycoalkaloids from Solanum sodomaeum," Planta Medica (1987), 53(1), pp. 59-62. (4 pages total).*
Rocca, M.A. Rev. Fac. Farm. Odont., Araraquara. 1976. vol. 10, No. 2, pp. 329-342—full English translation enclosed.*
2 pgs, "Chemical Investigation of the Berries of Solanum Aethiopicum," Banerjee, et al., Planta medica, vol. 25, 1974.
3 pgs, "Interactions between the Glycoalkaloids Solasonine and Solamargine in Relation to Inhibition of Fungal Growth," Fewell et al., Phytochemistry, vol. 37, No. 4, 1994.
1 pgs, "Isolation and Purification of Solasodine from Solanum Khasianum," Parmar, Indian Drugs, vol. 30, No. 12, 1993.
7 pgs, "OS Componentes Esteroidais Do Solanum Viarum, Dun," Rocca, Rev. Fac. Farm. Odont., Araraquara, vol. 10, No. 2, 1976 (no translation).

* cited by examiner

*Primary Examiner*—Christopher R. Tate
(74) *Attorney, Agent, or Firm*—Kagan Binder, PLLC

(57) ABSTRACT

The present invention relates to an improved extraction process for an alkaloid glycoside extract from the species *Solanum*. In this process, a ground, dried plant tissue of the species *Solanum* is subjected to alcohol extraction using methanol, the extract is dried and dissolved in a weak volatile acid and centrifuged, the supernatant is precipitated using a volatile base, and the precipitate is thoroughly washed and dried. Extracts having high purity, and products made by the process are also provided.

9 Claims, No Drawings

SOLVENT EXTRACTION PROCESS

The present invention relates to an improved extraction process for an alkaloid glycoside extract from the species *Solanum*.

A standard mixture of solasonine glycosides, isolated from the fruits of *Solanum sodomaem*, is known as BEC. BEC is a crude mixture of glycoalkaloids comprising the triglycerides solasonine (approx. 33%), solamargine (33%) and an undefined fraction which has been referred to as "di and monogylcosides".

The process for making BEC involves homogenizing the fruits of *Solanum sodomaem* in a large volume of acetic acid, filtering off the liquor through muslin, precipitating the glycosides with ammonia and repeating the steps several times (WO 00/6 11 53; Planta Medica 1987, 1: 59-62). The yield of the solasodine glycoside mixture is very low (approx. 0.8%).

BEC is incorporated in very small amounts into a topical cream (Curaderm®) which is used to treat skin lesions such as sunspots and keratosis.

BEC has also been reported to exhibit preferential cytotoxicity for various human cancer cells (WO 91/10743).

While BEC is of sufficient quality to be used in small quantities in over the counter (OTC) topical cream formulations, it does not meet the regulatory requirements for pharmaceutical use. Thus, the individual process steps of the standard process for the preparation of BEC are not defined to GMP (Good Manufacturing Process) in terms of scale up, definition of yield, composition and product quality.

Moreover, other than the presence of the triglycosides solasonine and solamargine the BEC mixture has never been analyzed regarding the precise nature of the active ingredients, the assumption being that all glycoside components are active in combination.

The present invention is directed towards a novel *solanum* glycoside extract comprising the active glycoside components in high purity meeting the requirements of GMP.

The present invention thus provides a novel extraction process for the preparation of a *solanum* glycoside extract consisting essentially only of the active *solanum* glycosides.

Also provided is a novel very sensitive HPLC method for the analysis of *solanum* glycoside extracts. This novel HPLC method employs an ACE 5 C18 (V99-140) column (length 25 cm+1 cm guard cartridge; particle size 5 µm; internal diameter 4.6 mm; pore size 100 Å), Advanced Chromatography Technologies (ACT) (obtainable from HiChrom, Theale).

The mobile phase used at a flow rate of 0.7 ml/min was 75% 20 mM (pH 2.95) phosphate buffer, 25% acetonitrile using a Spectra-Physics SP 8800 Ternary HPLC Pump. Detection was carried out at 205 nm with a Spectra-Physics, Spectra 1000 Variable Wavelength Detector.

Based on extensive analysis of the BEC mixture it was shown that in addition to the triglycosides solasonine and solamargine a diglycoside component is present in an amount of approximately 30%. It was surprisingly found that the diglyceride component does not appear to exhibit any activity in cytotoxicity in various experimental cancer cell lines.

In accordance with the present invention a solasodine glycoside extract is provided consisting essentially of the triglycerides solasonine and solamargine.

Preferably the extract is of close to 100% purity with no measurable or only trace amounts of the inactive diglycoside component.

Preferably, solasonine is present in the final extract in an amount between 30-50% whereas solamargine is present in an amount of 40-60%.

The extract of the present invention may be obtained by the following process:

The *solanum* plant tissue is dried and comminuted to a powder. The powder is subjected to an alcohol extraction. Following the removal of the alcohol the dried extract is dissolved in acid and centrifuged. The supernatant is precipitated under alkaline conditions. The acid/alkaline precipitation steps may be repeated several times.

The precipitate is then thouroughly washed with water and dried and further purified by silica gel chromatography.

As a *solanum* glycoside source any of the plants of the *Solanum* species may be used. Preferably, however, the extract of the invention is obtained from *Solanum sodomaem*. It has been found that the highest yields of the two components of the extract solamargine and solasonine may be obtained from the lyophilized fruit of *Solanum sodomaem*.

While the extraction process may be carried out using any pharmaceutically acceptable volatile alcohol including methanol, ethanol, propanol and isopropanol, the extraction is most preferably carried out using methanol.

For the precipitation step the dried extract may be treated with any volatile and weak acid and alkaline reagent. It has been found that optimal results may be obtained using acetic acid and concentrated ammonia.

For the chromatographic purification using silica gel chromatography, the freeze dried extract may be dissolved in methanol. Before elution the silica gel is washed with acetone. The elution is preferably carried out using a gradient of methanol and acetone.

In the subsequent example the extraction process of the invention is exemplified in detail below.

EXAMPLE 1

1.1 Preparation of Fruit

The fruits of *Solanum Sodomaem* were cut in half and dried by lyophilization. The dried fruits were then comminuted to a powder. The final dried, ground powder from a yield of 5 kg of fruits was 898 g.

1.2 Solvent Extraction of Glycoalkaloids

The powdered fruit (approx. 230 g each) was divided between 3 Soxhlet thimbles (Whatman cellulose, 60×180 mm), and four extractions conducted for each with 1 liter methanol (Labscan, HPLC grade). The first extraction (1 liter methanol) was conducted for 7.5 hours before the methanol was removed by evaporation and the resulting extracts analysed by HPLC. The 3 subsequent extractions were with 750 ml methanol to find the point at which all glycoalkaloids were completely extracted. The four extractions were labelled A, A1, A2 and A3, respectively. The concentrations of glycoalkaloid in the four separate extractions are shown in Table 1.

TABLE 1

Concentration of glycoalkaloids in the Extract

|  | Solasonine, mg/ml by HPLC | Solamargine, mg/ml by HPLC |
|---|---|---|
| A | 7.9 | 9.4 |
| $A_1$ | 2.2 | 2.6 |
| $A_2$ | 0.16 | 0.16 |
| $A_3$ | 0.06 | 0.07 |

1.3.1. Production Scale Purification of Extract A

The dry and partially evaporated extracts A, A1 and A2 (A3 abandoned due to lack of useful product) were pooled and evaporated to yield a pooled dry extract (62.23 g). The extracts were dissolved in acetic acid (2 liters, 3% (v/v)) and the slightly turbid solution clarified by centrifugation (6,000 rpm, 20 mins). The supernatant was collected and a small amount of green precipitate discarded. The sample was then filtered to remove a few small remaining lumps of green precipitate.

1.3.1.1 1$^{st}$ Precipitation with Ammonia

The filtrate was adjusted to pH 9 by addition of concentrated ammonia and the precipitate allowed to settle for 1 hour before centrifugation (6,000 rpm, 20 mins). This gave a gel-like precipitate, which was easily re-dissolved in approx. 1 liter 3% (v/v) acetic acid, such that the final volume of sample was 1.25 liters.

1.3.1.2 2$^{nd}$ Precipitation with Ammonia

The pH of the sample was adjusted to 9 by addition of concentrated ammonia and the precipitate was allowed to settle for a few minutes before centrifugation (6,000 rpm, 20 mins).

1.3.1.3 Washing of Precipitate

The precipitate was re-dispersed and thoroughly mixed with de-ionised water (6×250 ml), and collected by centrifugation. This procedure was repeated once and the pellets were drained.

1.3.1.4 Freeze-Drying of Product A

The pellets were dissolved in ammonium acetate, pH 4.5 (3% (v/v) acetic acid adjusted to pH 4.5 with concentrated ammonia to give a solution of ammonium acetate at pH 4.5). The final volume of solution at this stage was 360 ml. The sample was polish filtered through a glass fibre filter (Whatman GF/B) prior to weighing into plastic containers (16 cm×16 cm×6 cm). The sample was then frozen and subsequently freeze-dried.

The yield (by weight) of the extract was approx. 1.14% of the original weight of the whole fruit, or 6.45% of the dried powdered fruit.

The composition of the freeze dried extract was determined by HPLC. It was found to contain approx. 33% solasonine, 40.1% solamargine but no detectable traces of the diglycoside component.

1.4 The Freeze Dried Extract A

Chromatographic Purification of Extract A

A column was packed with dry Silica Gel (406.6 g, column dimensions: 7.5 cm×18 cm). Freeze-dried Extract A (13.59 g) was weighed out and dissolved in methanol (250 ml). Silica gel (106 g) was added, and the slurry was dried to a fine powder by evaporation. The slurry was then applied to the top of the silica column and a layer of silver sand was added (1 cm approx.). The column was washed with acetone (1 liter) before elution of the glycoalkaloids. The column was eluted at a flow rate of 1 liter/hr with a 4-step gradient of methanol:acetone as follows:

| | | |
|---|---|---|
| Step 1: | methanol (30% (v/v)):acetone (70% (v/v)), | 2 litres |
| Step 2: | methanol (40% (v/v)):acetone (60% (v/v)), | 2 litres |
| Step 3: | methanol (60% (v/v)):acetone (40% (v/v)), | 1 litre |
| Step 4: | methanol (100% (v/v)) | 1.5 litres |

1.4.1 Pooling of Fractions

Fractions (51×25 ml) were collected when step 1 of the gradient was applied, in order to monitor where the solamargine and solasonine started to elute. After this, larger 500 ml fractions were collected throughout until after step 4. The progress of the purification was monitored be TLC. Fractions containing the desired endproducts (solamargine, solamargine plus solasonine, as well as the solasonine) were pooled. The fractions were dried by rotary evaporation and processed immediately as described below.

1.4.2 Ammonia Precipitation

The dried pooled fractions were dissolved in acetic acid (900 ml, 3% (v/v)) and adjusted to pH 9 by addition of concentrated ammonia. The resulting precipitate was collected by centrifugation (6,000 rpm/20 mins).

1.4.3 Washing of Precipitates and Freeze-Drying

The resulting precipitate was washed three times with water, collected by centrifugation, and frozen at −20° C., prior to re-dissolution in acetic acid (1.6 liters, 0.1% (v/v)). The sample was then divided equally into 8 containers and freeze-dried.

1.4.4 Yields and Purities of Final Purified Products

The freeze-dried products were weighed and stored desiccated under vacuum at +4° C. The samples were then analysed for purity (against a BEC standard) by HPLC. The results are presented in Table 2.

TABLE 2

Yields and Purities of Final product

| Sample | Yield G | *% recovery | HPLC Analysis % Solasonine | % Solamargine | % Total by HPLC |
|---|---|---|---|---|---|
| A | 8.49 | 88.0 | 40.5 | 55.3 | 97.5 |

1.5 Chemical and Microbiological Analysis of Original BEC Plant Extract and Final Product Prepared in Accordance with the Invention Samples of the prior art BEC product as well as a product in accordance with the present invention were analysed for moisture content and for microbial, pesticide and heavy metal content.

1.5.1 Microbial Analysis

A sample of the prior art BEC product, together with the final purified product of the invention were sent for microbial analysis, moisture, methanol, ash and heavy metal analysis.

Results for these analyses are summarised in Table 3.

TABLE 3

Summary of analytical results for BEC plant material and Purified product A

| Test | BEC product | A |
|---|---|---|
| Bacterial count | >1500 per 50 mg | <1 per 10 mg |
| Fungal Count | >1500 per 50 mg | <1 per 10 mg |
| Residue on ignition, % | 6.7 | 0.4 |
| Water, % m/m | 1.99 | 5.66 |
| Methanol, μg/g | 350 | <50 |
| Heavy metals, ppm as Pb | 10 | <10 |

TABLE 3-continued

Summary of analytical results
for BEC plant material and Purified product A

| Test | BEC product | A |
|---|---|---|
| Heavy Metals: | | |
| Cd, mg/kg | | <0.02 |
| Pb, mg/kg | | <0.10 |
| Hg, mg/kg | | 0.01 |
| As, mg/kg | | 0.03 |

2. CONCLUSIONS

Solvent extraction using methanol has proven to be very successful in the extraction of the selective triglycosides solasonine and solamargine with little or no contamination with the diglycoside.

In order to obtain the final high purity product the extract was subjected to a silica gel chromatography. Preferably, in order to optimize the recovery of solasonine, which has a low solubility in acetone, a graded eluent comprising methanol and acetone should be applied.

It was shown that the process of the present invention effectively removes the third component which is present in BEC in amounts in excess of 30%.

Following evaporation of the solvent from the sample, a single re-precipitation with ammonia and washing gives rise to a clean product, which can easily be freeze-dried from solution in aqueous ammonium acetate. The volatile constituents are removed during the freeze-drying process. It is preferable that the final purification step is carried out within a 24 hour period in order to optimise the appearance of the final product.

2.1 Product Purity

The process developed here gives a significantly improved product compared with that obtained by the Cham process (2), in terms of its appearance, purity, moisture, and heavy metal content. The final freeze-dried product was a granular off-white powder. The purity of the product was in the range 92.7-99.3% (HPLC analysis), compared with a typical purity of 65-70% obtained by the previous method. Moisture content was also lower (4.0-5.7% compared with 7% obtained previously), and heavy metal contamination was extremely low.

The invention claimed is:

1. A process for the isolation of an extract of solasonine and solamargine comprising the following steps:
    a) ground, dried plant tissue of a *Solanum* species is subjected to alcohol extraction using methanol;
    b) the extract obtained is dried and dissolved in a weak volatile acid and centrifuged to provide a supernatant;
    c) the supernatant is precipitated using a volatile base, thereby providing a precipitate;
    d) the precipitate is washed and dried; and
    e) the precipitate as obtained in step d is subjected to silica gel chromatography to provide an extract comprising 30-50% of solasonine and 40-60% of solamargine, the extract comprising a combination of solasonine and solamargine above 90%.

2. A process according to claim 1, wherein the steps b) and c) are repeated a plurality of times.

3. The process according to claim 1, wherein the volatile acid is acetic acid.

4. The process according to claim 1, wherein the base is concentrated ammonia.

5. The process of claim 1, wherein the dried plant tissue is lyophilized fruit of *Solanum sodomaeum*.

6. The process according to claim 1, wherein the silica gel chromatography step e) uses an eluent that is a methanol/acetone gradient.

7. An isolated extract of solasonine and solamargine prepared by the process of claim 1.

8. The extract of claim 7, wherein solasonine and solamargine are present in a ratio of solasonine:solamargine of 0.3-0.7:0.4-0.8.

9. The extract of claim 7, wherein solasonine and solamargine are present in a ratio of solasonine:solamargine of 0.4-0.6:0.5-0.7.

* * * * *